(12) United States Patent  
Hyun

(10) Patent No.: US 9,047,394 B2
(45) Date of Patent: Jun. 2, 2015

(54) 3D ULTRASOUND SYSTEM FOR INTUITIVE DISPLAYING TO CHECK ABNORMALITY OF OBJECT AND METHOD FOR OPERATING 3D ULTRASOUND SYSTEM

(75) Inventor: Dong-gyu Hyun, Gwangju-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 25 days.

(21) Appl. No.: 13/243,674

(22) Filed: Sep. 23, 2011

(65) Prior Publication Data

US 2012/0101383 A1    Apr. 26, 2012

(30) Foreign Application Priority Data

Oct. 22, 2010    (KR) .................. 10-2010-0103448

(51) Int. Cl.
*A61B 8/00* (2006.01)
*G06F 19/00* (2011.01)
*A61B 5/107* (2006.01)
*A61B 8/08* (2006.01)
(Continued)

(52) U.S. Cl.
CPC ............ *G06F 19/321* (2013.01); *A61B 5/1072* (2013.01); *A61B 8/0866* (2013.01); *A61B 8/461* (2013.01); *A61B 8/483* (2013.01); *A61B 8/5223* (2013.01); *A61B 2503/02* (2013.01); *G06F 19/345* (2013.01); *G01S 7/52071* (2013.01); *G06T 7/0012* (2013.01); *G06T 2207/10136* (2013.01); *G06T 2207/30044* (2013.01); *A61B 8/466* (2013.01)

(58) Field of Classification Search
CPC ... G06F 19/345; G06F 19/321; A61B 8/0866; A61B 8/461; A61B 8/483; A61B 8/5223; A61B 5/1072; A61B 2503/02; G06T 7/0012; G06T 2207/10136; G06T 2207/30044; G01S 7/52071
USPC .................. 600/437–447, 449–452, 459–461
See application file for complete search history.

(56) References Cited

U.S. PATENT DOCUMENTS

| 7,252,638 B2 * | 8/2007 | Kahn et al. ..................... 600/443 |
| 2004/0068166 A1 * | 4/2004 | Faulkner et al. .............. 600/407 |
| 2007/0073147 A1 | 3/2007 | Holladay et al. |

(Continued)

FOREIGN PATENT DOCUMENTS

| JP | 2006-247206 A | 9/2006 |
| KR | 10-2008-0004775 A | 1/2008 |

(Continued)

OTHER PUBLICATIONS

Pandya, P. P., et al., "Screening for fetal trisomies by maternal age and fetal nuchal translucency thickness at 10-14 weeks of gestation", British Journal of Obstetrics and Gynaecology, Dec. 1, 1995, pp. 957-962, vol. 102 No. 12.

(Continued)

*Primary Examiner* — Elmer Chao
(74) *Attorney, Agent, or Firm* — McDermott Will & Emery LLP

(57) ABSTRACT

Provided are a three-dimensional (3D) ultrasound system and a method for operating the 3D ultrasound system, which are capable of intuitively displaying the abnormality of an object by determining a grade by comparing measurement data obtained by measuring ultrasound data relating to the object and displaying the measurement data in a different way based on the determined grade.

12 Claims, 4 Drawing Sheets

FIG. 3

(51) Int. Cl.
*G06T 7/00* (2006.01)
*G01S 7/52* (2006.01)

(56) References Cited

U.S. PATENT DOCUMENTS

2008/0077014 A1* 3/2008 Krantz et al. ............... 600/443
2009/0012432 A1* 1/2009 Sharf ........................... 600/588

FOREIGN PATENT DOCUMENTS

KR          10-1024857 B1     3/2011
WO     WO 2009/136332 A2    11/2009

OTHER PUBLICATIONS

First-Trimester Risk Assessment, GE Healthcare, Jan. 1 2006, 8 pages, Retrieved from the Internet: URL:http://www.gehealthcare.com/usen/ultrasound/education/docs/TRImester_CSpages.pdf, Retrieved on Jan. 4, 2012.
Braithwaite, J. M., et al., "Nuchal translucency measurements: frequency distribution and changes with gestation in a general population", British Journal of Obstetrics and Gynaecology, Dec. 1996, pp. 1201-1204, vol. 103.
Moratalla, J., et al., "Semi-automated system for measurement of nuchal translucency thickness", Ultrasound in Obstetrics and Gynecology, Oct. 1, 2010, vol. 36 No. 4, pp. 412-416.
Extended European Search Report, issued in European Patent Application No. 11 182 839.8, dated Jan. 18, 2012.
Korean Office Action issued in Korean Application No. 10-2011-0108811 dated Jun. 10, 2014, w/English translation.
Korean Office Action issued in Korean Application No. 2011-0108811, dated Jan. 26, 2015, with English translation.
Korean Office Action issued in Korean Application No. 2011-0108811, dated Mar. 31, 2015, 6 pages with English translation.

* cited by examiner

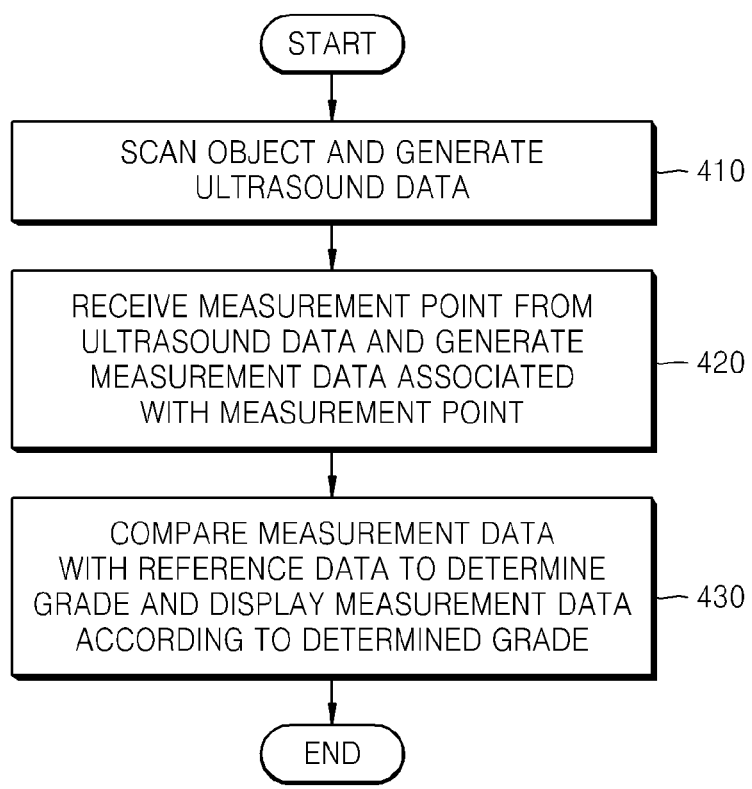

3D ULTRASOUND SYSTEM FOR INTUITIVE DISPLAYING TO CHECK ABNORMALITY OF OBJECT AND METHOD FOR OPERATING 3D ULTRASOUND SYSTEM

CROSS-REFERENCE TO RELATED PATENT APPLICATION

This application claims the benefit of Korean Patent Application No. 10-2010-0103448, filed on Oct. 22, 2010, in the Korean Intellectual Property Office, the disclosure of which is incorporated herein in its entirety by reference.

BACKGROUND

The present invention relates to a method for intuitively checking the abnormality of an object.

Ultrasound systems transmit ultrasound signals from a surface of a human body or an animal body towards a predetermined part within the body (i.e., an object such as a fetus or internal organ) and use information about ultrasound signals reflected from a tissue within the body to obtain images related to a cross-section of a soft tissue or blood flow. Due to its compact and cheap design, real-time display, and high stability with no risk of exposure to X-rays or other radiations, such an ultrasound system has been widely used together with other image diagnostic devices such as an X-ray diagnostic device, a Computerized Tomography (CT) scanner, a Magnetic Resonance Image (MRI) device, and a nuclear medicine diagnostic device, A common method for detecting a fetus with Down syndrome is to measure the thickness of a nuchal translucency (NT) in the fetus using an ultrasound system. According to this method that was devised by Nicolaides in 1992, if it is determined that a fetus has any abnormality, an NT thickness has increased due to subcutaneous accumulation of fluid at the back of a fetal neck.

In particular, a fetus with Down syndrome or other chromosomal abnormalities, or heart defects may usually have an increased NT. Thus, when a doctor measures the thickness of a translucent space behind a fetal neck using an ultrasound system and finds that the thickness of the translucent space exceeds 2.5 mm, a more accurate test, such as chorionic villus sampling or amniocentesis, is performed to see whether a fetus has an abnormality.

However, this approach has a problem that it is difficult to accurately measure the thickness of an NT because it may vary depending on an angle or measurement method. Thus, a doctor is inconvenienced in having to check whether an actual NT thickness is greater than 2.5 mm for each test before making conclusions about the abnormality of a fetus.

SUMMARY

The present invention provides a three-dimensional (3D) ultrasound system and a method for operating the 3D ultrasound system, which are capable of intuitively displaying the abnormality of an object by generating measurement data using ultrasound data relating to the object, comparing the measurement data with reference data, and controlling a color of the measurement data according to the comparison result.

The present invention also provides a 3D ultrasound system and a method for operating the 3D ultrasound system, which allow a more intuitive display of the degree of severity of an abnormality in an object by displaying measurement data in different colors that are allocated depending on whether a Nuchal Translucency (NT) thickness measured on the object is in an abnormal, warning, or normal range.

According to an aspect of the present invention, there is provided a 3D ultrasound system including: a scanning unit configured to scan an object and generate ultrasound data; a measuring unit configured to receive an input of a measurement point in the ultrasound data and generate measurement data associated with the measurement point; and a display controller configured to compare the measurement data with reference data, determine a grade, and display the measurement data based on the determined grade.

The display controller may be configured to display the measurement data in a color allocated to the determined grade.

If the object is a fetus and the measurement point is input with respect to a Nuchal Translucency (NT) of the fetus, the measuring unit may be configured to generate two measurement lines corresponding to the NT of the fetus, measure a distance between the two measurement lines as a measured length of the NT and generate measurement data including the measured length.

The reference data may include a plurality of standard length ranges one to one corresponding to fetal ages.

In this case, the display controller may be configured to analyze an age of the fetus based on the ultrasound data, extract from the plurality of standard length ranges a first standard length range corresponding to the age that is obtained from the analysis, compare the first standard length range with the measured length in the measurement data and determine the grade.

Furthermore, if the reference data includes a measurement statistical distribution for the measurement point, the display controller may be configured to check a point in the measurement statistical distribution at which the measurement data is located and determine one of an abnormal grade, a warning grade, and a normal grade.

In this case, if the point is in a warning interval within the measurement statistical distribution and determined to correspond to the 'warning grade', the display controller may be configured to display the measurement data by adjusting the luminance of a color allocated to the warning grade based on a distance between the point and one of abnormal and normal intervals within the measurement statistical distribution.

The 3D ultrasound system may further include an alarm output unit configured to output an alarm if the point is in one of abnormal and warning intervals within the measurement statistical distribution and determined to correspond to one of the abnormal and warning grades.

According to another aspect of the present invention, there is provided a method for operating a 3D ultrasound system, including: scanning an object and generating ultrasound data; receiving an input of a measurement point from the ultrasound data and generating measurement data associated with the measurement point; comparing the measurement data with selected reference data and determining a grade; and displaying the measurement data based on the determined grade.

The 3D ultrasound system and the method for operating the 3D ultrasound system are capable of intuitively displaying the abnormality of an object by generating measurement data using ultrasound data relating to the object, comparing the measurement data with reference data, and controlling a color of the measurement data based on the comparison result.

According to an embodiment of the present invention, measurement data is displayed in different colors that are allocated depending on whether an NT thickness measured with respect to the object is in an abnormal, warning, or normal range, thereby allowing more intuitive display of the degree of severity according to the presence of abnormality in the object.

BRIEF DESCRIPTION OF THE DRAWINGS

The above and other features and advantages of the present invention will become more apparent by describing in detail exemplary embodiments thereof with reference to the attached drawings in which:

FIG. 5 is a flowchart illustrating a method for operating a 3D ultrasound system of FIG. 1, according to an embodiment of the present invention.

DETAILED DESCRIPTION OF THE EMBODIMENTS

Figure 1:
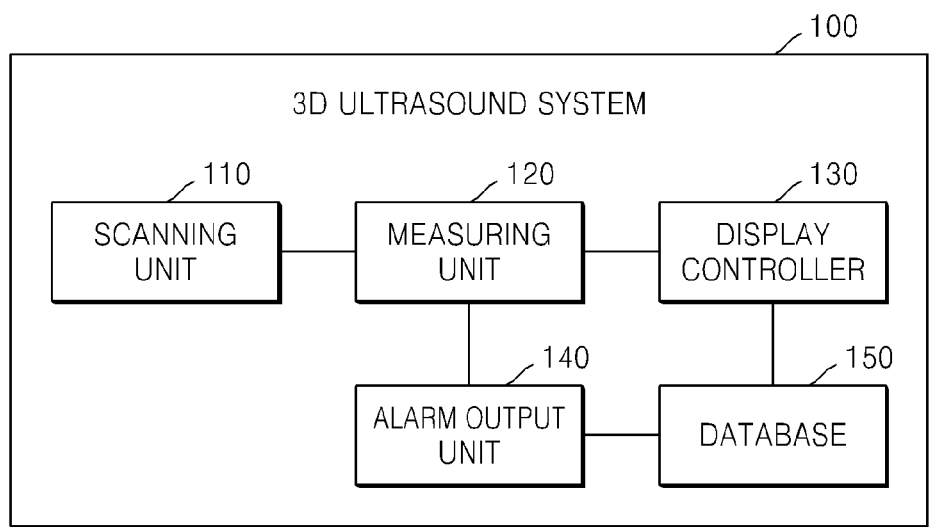
FIG. 1 illustrates an internal configuration of a three-dimensional (3D) ultrasound system according to an embodiment of the present invention.

Hereinafter, embodiments of the present invention will be described in detail with reference to the attached drawings. The present invention is not restricted or limited by the following embodiments. In the drawings, like reference numerals refer to like elements.

FIG. 1 illustrates an internal configuration of a three-dimensional (3D) ultrasound system 100 according to an embodiment of the present invention.

Referring to FIG. 1, the 3D ultrasound system 100 includes a scanning unit, a measuring unit 120, a display controller 130, an alarm output unit 140, and a database 150.

The scanning unit 110 scans an object to generate ultrasound data. More specifically, the scanning unit 110 generates ultrasound data including image data obtained by scanning the object within a human body or an animal body. The object within the human body or the animal body may be a fetus and its internal organs. In other words, the scanning unit 110 generates ultrasound data by scanning the fetus and its internal organs.

In order to generate ultrasound data for an object, the scanning unit 110 may set a region of interest (ROI) on the object and locates a seed in the ROI. The seed may be set by an observer. Otherwise, the seed may be automatically set based on the ROI.

When the object is a fetus, the seed may be located near a Nuchal Translucency (NT) of the fetus. Thereafter, the scanning unit 110 performs a 3D ultrasound scan on the object to generate image data such that the ultrasound data may be generated. The image data corresponds to a region in the ultrasound data occupied by the object.

The measuring unit 120 receives an input of a measurement point from the ultrasound data and generates measurement data associated with the measurement point. In this case, the measurement point may be interpreted as a 'seed'.

Figure 2:
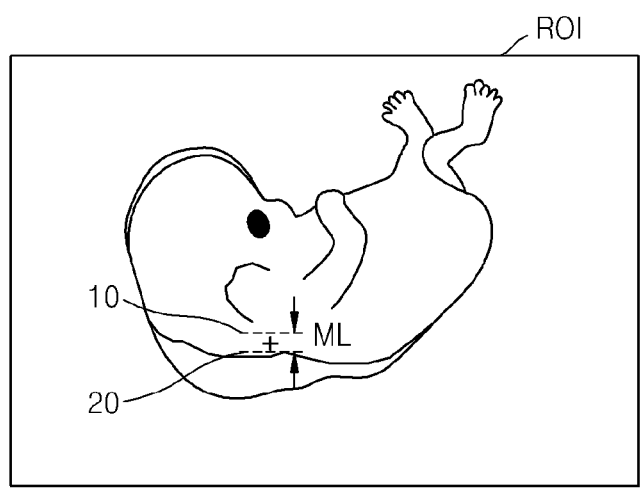
FIG. 2 illustrates an example of an ROI when an object is a fetus.

FIG. 2 illustrates an example of an ROI when an object is a fetus.

Referring to FIGS. 1 and 2, when the object is a 'fetus', the measuring unit 120 may receive as an input a measurement point + around an NT of the fetus. The measuring unit 120 may generate two measurement lines 10, 20 corresponding to the NT of the fetus around the measurement point +. The measuring unit 120 may measure a distance between the two measurement lines 10, 20 as a measured length ML of the NT.

The two measurement lines 10, 20 may be generated by various methods. For one example, the measuring unit 120 may recognize the NT of the fetus around the measurement point + based on the characteristics of the fetal NT, and generate the two measurement lines 10, 20 corresponding to the fetal NT. In this case, the measuring unit 120 can recognize the fetal NT based on brightness difference of pixels around the measurement point +.

For another example, an observer, e.g., a doctor, may input positions of the two measurement liens 10, 20 to generate the two measurement lines 10, 20.

However, a method for obtaining the measured length ML according to FIG. 2 is an example, and the measured length ML of the NT may be measured by various methods.

In this case, the measuring unit 120 generates measurement data including the measured length ML.

A common method for detecting a fetus with Down syndrome is to measure the thickness of an NT of a fetus. A fetus having Down syndrome or other chromosomal abnormalities, or heart defects may usually have a thick NT. Thus, when a doctor measures the thickness of a translucent space behind a fetal neck using an ultrasound system and finds that the thickness of the translucent space is greater than 2.5 mm, a more accurate test such as chorionic villus sampling or amniocentesis is performed to check whether a fetus has an abnormality.

However, because an NT thickness used in detecting a fetus with Down syndrome varies depending on the age of a fetus, it is necessary to set a standard length range for future use so as to determine whether a fetus has an abnormality by comparing a measured length obtained by measuring an actual object with a standard length range.

The display controller 130 compares the measurement data with reference data to determine a grade and displays the measurement data based on the determined grade. For example, the reference data may contain a standard NT length range for each fetal age. In other words, the reference data may include a plurality of standard length ranges one to one corresponding to the fetal ages.

The display controller 130 analyzes an age of the fetus, extracts from the reference data a standard length range corresponding to the age which is obtained from the analysis, and compares the standard length range with the measured length ML in the measurement data. The display controller 130 then determines a grade depending on whether the measured length ML is less or greater than the standard length range, and displays the measurement data in a color that is allocated to the determined grade.

Figure 3:
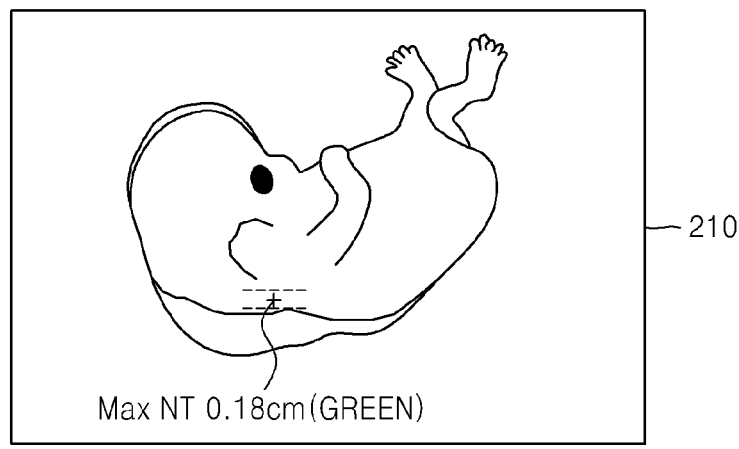
FIG. 3 illustrates an example of displaying measurement data obtained from an object.
Figure 3:
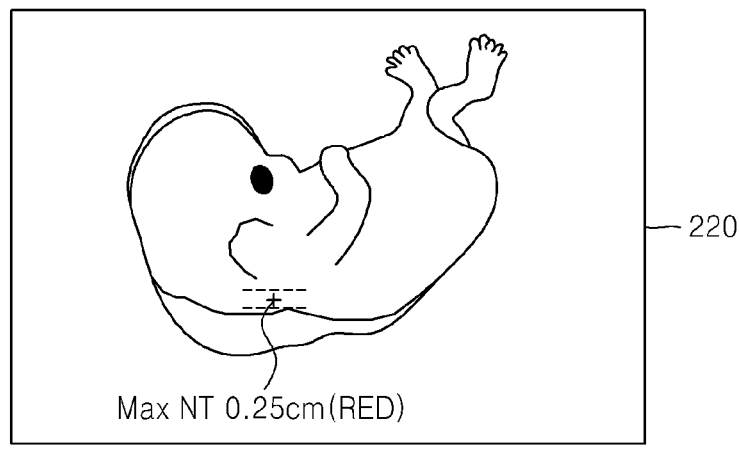
Figure 3:
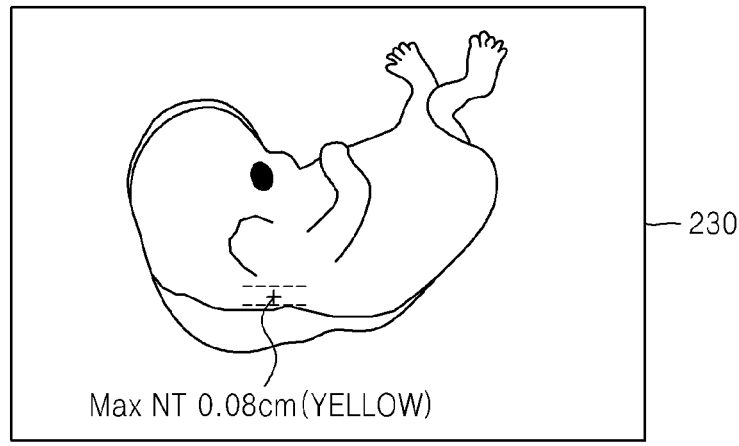

FIG. 3 illustrates an example of displaying measurement data obtained from an object.

Referring to FIGS. 1 through 3, when a measured length ML in measurement data is included in a standard length range extracted from reference data for the age of an object, e.g., a fetus, the display controller 130 displays the measurement data (MaxNT 0.18 cm) around a measurement point + in a green color image 210. The measured length ML that is included in the standard length range may indicate that the fetus corresponds to a 'normal grade'.

When the measured length ML is greater than the standard length range extracted from reference data, the display controller 130 displays the measurement data (MaxNT 0.25 cm) around the measurement point + in a red color image 220. The measured length ML that is greater than the standard length range may indicate that the fetus has Down syndrome and corresponds to an 'abnormal grade'. Thus, the display controller 130 may display the measurement data (MaxNT 0.25 cm) in the red color image 220 so that a doctor may intuitively check for the abnormality of the fetus, thereby allowing a doctor to easily recognize the severity of the abnormality of the fetus.

Conversely, when the measured length ML is less than the standard length range extracted from reference data, the display controller 130 displays the measurement data (MaxNT 0.08 cm) around the measurement point + in a yellow color image 230. The measured length ML that is less than the standard length range may indicate that the fetus corresponds to a 'warning grade'.

When the fetus is determined to correspond to the 'abnormal grade' or the 'warning grade', the alarm output unit 140 outputs an alarm.

In order to facilitate the detection of a fetus having Down syndrome, the 3D ultrasound system 100 needs to have reference data to compare with measurement data for future use. The reference data may contain a measurement statistical distribution for the measurement point. A doctor uses statistical data created from many years of experience and experimental values to obtain standard NT length ranges for each age level.

For example, the doctor may create statistical data using ultrasound data obtained from fetuses for each age level and compare ultrasound data obtained from a fetus with statistical data in order to determine the age of the fetus. The statistical data and the reference data may be stored in the database 150.

For example, the database 150 may contain reference data and statistical data for each age level.

Figure 4:
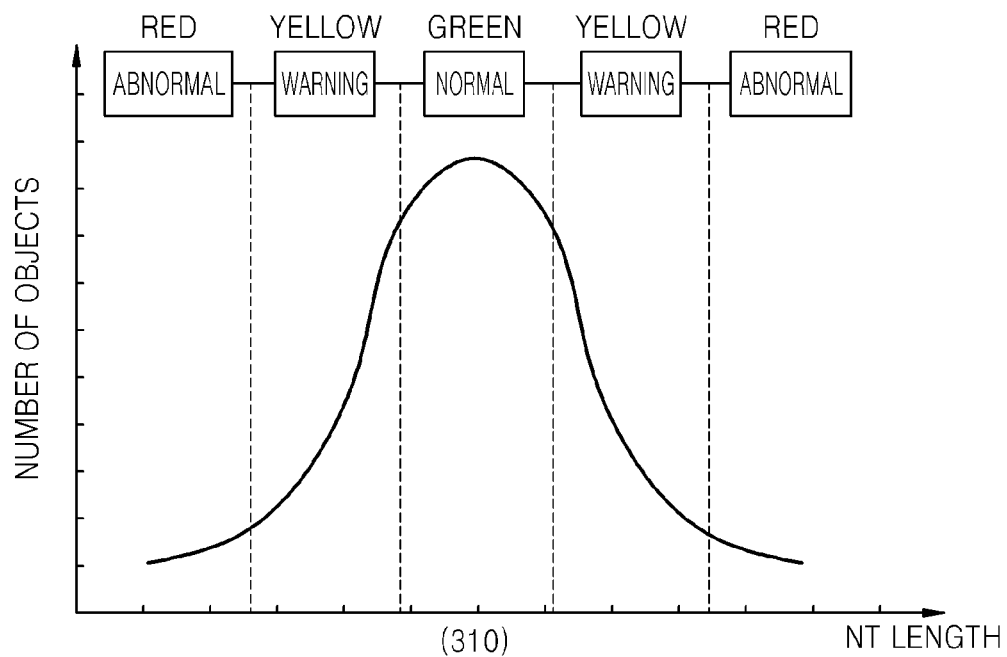
FIG. 4 illustrates an example of reference data including a measurement statistical distribution.
Figure 4:
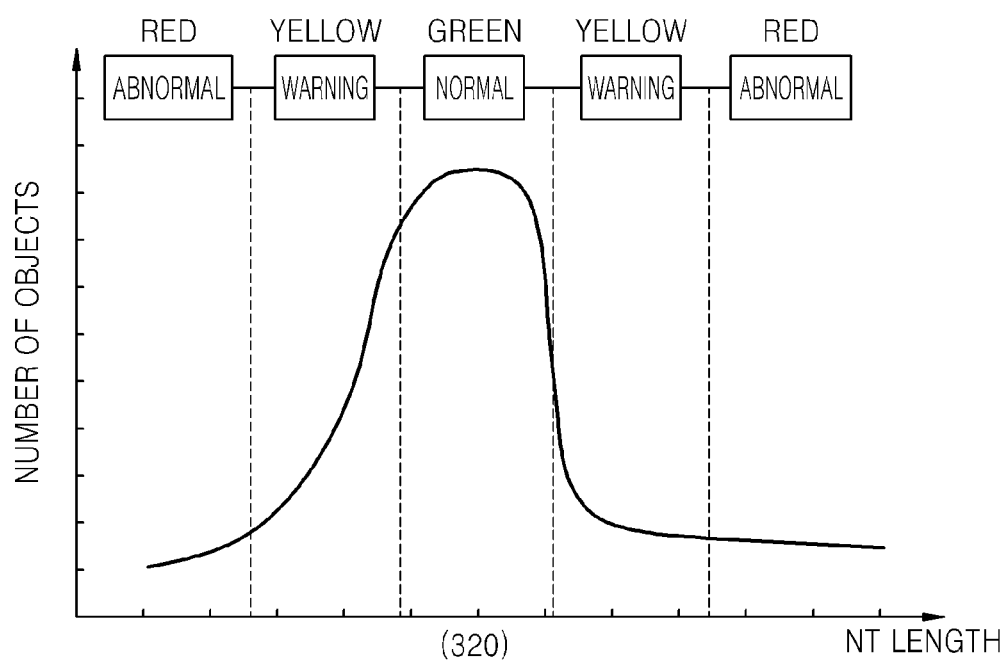

FIG. 4 illustrates an example of reference data including a measurement statistical distribution.

Referring to FIGS. 1, 2 and 4, the reference data includes the measurement statistical distributions for each of ages where an x-axis represents an NT length and a y-axis represents the number of objects (fetuses). The measurement statistical distributions may vary depending on ages 310 and 320. In other words, although numeric values are not described in detail in FIG. 4, an NT length may vary depending on ages.

Thus, the display controller 130 analyzes the age of the fetus based on the ultrasound data, extracts reference data corresponding to the determined age from the database 150, and compares a standard length range in the extracted reference data with a measured length ML in the measurement data.

In one embodiment, the display controller 130 checks a point in the measurement statistical distribution at which the measurement data, e.g., the measured length ML, is located and determines one of an abnormal grade, a warning grade, and a normal grade. When the point is in a normal interval (including the largest number of objects) within the measurement statistical distribution and the fetus is determined to correspond to a normal grade, the display controller 130 may display the measurement data in 'green'.

When the point is in a warning interval (including an increasing or decreasing number of objects) within the measurement statistical distribution and the fetus is determined to correspond to a warning grade, the display controller 130 may display the measurement data in 'yellow'.

When the point is in an abnormal interval (with the smallest number of objects) within the measurement statistical distribution and the fetus is determined to correspond to an abnormal grade, the display controller 130 may display the measurement data in 'red'.

Furthermore, when the point is in the warning interval and the fetus is determined to correspond to the 'warning grade', the display controller 130 may display the measurement data by adjusting the luminance of the color allocated to the warning grade based on a distance between the point and one of abnormal and normal intervals within the measurement statistical distribution. In other words, when the point is located at a position in the warning interval that is closer to one of the normal and abnormal intervals, the display controller 130 may display the measurement data in different colors such as dark or light yellow.

When the point is in an abnormal or warning interval within the measurement statistical distribution and determined to correspond to the abnormal or warning grade, the alarm output unit 140 outputs an alarm.

FIG. 5 is a flowchart illustrating a method for operating the 3D ultrasound system 100 of FIG. 1, according to an embodiment of the present invention.

Referring to FIGS. 1, 2 and 5, in operation 410, the 3D ultrasound system 100 scans an object to generate ultrasound data. More specifically, the 3D ultrasound system 100 scans a fetus and its internal organs as an object to obtain image data and generates ultrasound data including the obtained image data.

In operation 420, the 3D ultrasound system 100 receives an input of a measurement point + in the ultrasound data and generates measurement data associated with the measurement point +. For example, if the object is a fetus and the measurement point + is input with respect to an NT of the fetus, the 3D ultrasound system 100 measures a measured length ML of the NT based on the measurement point + and generates measurement data including the measured length ML.

In operation 430, the 3D ultrasound system 100 compares the measurement data with reference data to determine a grade and displays the measurement data based on the determined grade. In other words, the 3D ultrasound system 100 may display the measurement data in a color allocated for the determined grade.

In one embodiment, the reference data may contain standard NT lengths for each of ages. The 3D ultrasound system 100 analyzes the age of the fetus based on the ultrasound data, extracts from the reference data a standard length range corresponding to the age which is obtained from the analysis, and compares the standard length range with the a measured length ML in the measurement data. The age of the fetus may be analyzed by comparing statistical data stored in the database 150 with the ultrasound data. The 3D ultrasound system 100 determines a grade depending on whether the measured length ML is less or greater than the standard length range and displays the measurement data in a color that is allocated to the determined grade.

Alternatively, if the reference data contains a measurement statistical distribution for the measurement point +, the 3D ultrasound system 100 may check a point in the measurement statistical distribution at which the measurement data is located and determine one of an abnormal grade, a warning grade, and a normal grade. The 3D ultrasound system 100 may then display the measurement data in one of red, yellow and green colors that is allocated for the determined grade.

For example, if the point is in the warning interval within the measurement statistical distribution and is determined to correspond to the 'warning grade', the 3D ultrasound system 100 may display the measurement data by adjusting the luminance of the color allocated to the warning grade based on a distance between the point and one of the abnormal and normal intervals within the measurement statistical distribution.

Alternatively, if the point is in the abnormal or warning interval within the measurement statistical distribution and is determined to correspond to the abnormal or warning grade, the 3D ultrasound system 100 may output an alarm.

Embodiments of the present invention can include a computer readable medium including program commands for executing operations implemented through various computers. The computer readable medium can store program commands, data files, data structures or combinations thereof. The program commands recorded in the medium may be specially designed and configured for the present invention or be known to those skilled in the field of computer software. Examples of a computer readable recording medium include magnetic media such as hard disks, floppy disks and magnetic tapes, optical media such as CD-ROMs and DVDs, magneto-optical media such as floptical disks, or hardware devices such as ROMs, RAMS and flash memories, which are specially configured to store and execute program commands. Examples of the program commands include a machine language code created by a compiler and a high-level language code executable by a computer using an interpreter and the like.

While the present invention has been particularly shown in the drawings and described with reference to specific components and exemplary embodiments thereof, It should be understood that the exemplary embodiments described therein should be considered in a descriptive sense only and not for purposes of limitation. It will be understood by those of ordinary skill in the art that various changes in form and details may be made therein without departing from the spirit and scope of the present invention as defined by the following claims. Therefore, the scope of the invention is defined not by the detailed description of the invention but by the appended claims, and all differences within the scope of the appended claims and their equivalents will be construed as being included in the present invention.

What is claimed is:

1. A three-dimensional (3D) ultrasound system comprising:
   a scanning unit configured to scan an object and generate ultrasound data;
   a measuring unit configured to receive an input of a measurement point in the ultrasound data and generate measurement data associated with the measurement point,
   wherein the measurement point is input with respect to a Nuchal Translucency (NT) of a fetus, and
   the measuring unit is configured to generate two measurement lines corresponding to the NT of the fetus, measure a distance between the two measurement lines as a measured length of the NT, and generate the measurement data including the measured length; and
   a display controller configured to compare the measurement data with reference data, determine a grade, and display the measurement data based on the determined grade,
   wherein the reference data include a plurality of standard length ranges corresponding one to one to fetal ages,
   wherein the display controller is configured to determine an age of the fetus based on the ultrasound data, extract from the plurality of standard length ranges a first standard length range corresponding to the determined age of the fetus, and compare the first standard length range with the measurement data to determine the grade based on whether the measurement data is included in the standard length range, is greater than the standard length range, or is less than the standard length range,
   wherein the display controller is configured to display the measurement data in more than one color allocated to the determined grade, and the determined grade is selected from one of an abnormal grade, a warning grade, and a normal grade, and
   wherein each of the abnormal grade, warning grade, and normal grade correspond to a different display color.

2. The system of claim 1, wherein the display controller is configured to compare the first standard length range with the measured length in the measurement data and determine the grade.

3. The system of claim 1, wherein if the reference data includes a measurement statistical distribution for the measurement point, and
   wherein the display controller is configured to check a point in the measurement statistical distribution at which the measurement data is located and determine one of the abnormal grade, the warning grade, and the normal grade.

4. The system of claim 3, wherein if the point is in a warning interval within the measurement statistical distribution and determined to correspond to the 'warning grade', the display controller is configured to display the measurement data by adjusting the luminance of a color allocated to the warning grade based on a distance between the point and one of abnormal and normal intervals within the measurement statistical distribution.

5. The system of claim 3, further comprising an alarm output unit configured to output an alarm if the point is in one of abnormal and warning intervals within the measurement statistical distribution and determined to correspond to one of the abnormal and warning grades.

6. A method for operating a three-dimensional (3D) ultrasound system, the method comprising:
   scanning an object and generating ultrasound data;
   receiving an input of a measurement point in the ultrasound data and generating measurement data associated with the measurement point,
   wherein the measurement point is input with respect to a Nuchal Translucency (NT) of a fetus, and
   the generating of the measurement data associated with the measurement point comprises:
      generating two measurement lines corresponding to the NT of the fetus;
      measuring a distance between the two measurement lines as a measured length of the NT; and
      generating the measurement data including the measured length;
   comparing the measurement data with reference data and determining a grade; and
   displaying the measurement data based on the determined grade,
   wherein the reference data include a plurality of standard length ranges corresponding one to one to fetal ages, and
   wherein the displaying of the measurement data based on the determined grade comprises:
      determining an age of the fetus based on the ultrasound data;
      extracting from the plurality of standard length ranges a first standard length range corresponding to the determined age of the fetus; and
      comparing the first standard length range with the measurement data to determine the grade based on whether the measurement data is included in the standard length range, is greater than the standard length range, or is less than the standard length range, wherein the displaying of the measurement data based on the determined grade comprises:
  displaying the measurement data in more than one color allocated to the determined grade, and
  selecting the determined grade from one of an abnormal grade, a warning grade, and a normal grade,
wherein each of the abnormal grade, warning grade, and normal grade correspond to a different display color.

7. The method of claim 6, wherein the displaying of the measurement data based on the determined grade comprises comparing the first standard length range with the measured length in the measurement data.

8. The method of claim 6, wherein when the reference data includes a measurement statistical distribution for the measurement point, the displaying of the measurement data based on the determined grade comprises checking a point in the measurement statistical distribution at which the measurement data is located and determining one of the abnormal grade, the warning grade, and the normal grade.

9. The method of claim 8, wherein if the point is in a warning interval within the measurement statistical distribution and determined to correspond to the 'warning grade', the displaying of the measurement data based on the determined grade comprises displaying the measurement data by adjusting the luminance of a color allocated to the warning grade based on a distance between the point and one of abnormal and normal intervals within the measurement statistical distribution.

10. The method of claim 8, further comprising outputting an alarm if the point is in one of abnormal and warning intervals within the measurement statistical distribution and determined to correspond to one of the abnormal and warning grades.

11. The system of claim 1, wherein the display controller determines the age of the fetus by comparing the ultrasound data with statistical data obtained from fetuses of different fetal ages.

12. The method of claim 6, wherein the determining the age of the fetus comprises comparing the ultrasound data with statistical data obtained from fetuses of different fetal ages.

* * * * *